(12) United States Patent
Gudmundsson

(10) Patent No.: US 6,471,988 B1
(45) Date of Patent: Oct. 29, 2002

(54) DEVICE FOR PROTECTION AGAINST THE SUN AND APPLICATION OF SUBSTANCE TO THE SKIN

(75) Inventor: Fredrik Gudmundsson, Goteborg (SE)

(73) Assignee: Medeikonos AB, Goteborg (SE)

( * ) Notice: Subject to any disclaimer, the term of this patent is extended or adjusted under 35 U.S.C. 154(b) by 0 days.

(21) Appl. No.: 09/720,083

(22) PCT Filed: Jun. 24, 1999

(86) PCT No.: PCT/SE99/01154
§ 371 (c)(1),
(2), (4) Date: Feb. 26, 2001

(87) PCT Pub. No.: WO00/00248
PCT Pub. Date: Jan. 6, 2000

(30) Foreign Application Priority Data

Jun. 26, 1998 (SE) ............................................. 9802278

(51) Int. Cl.⁷ ................................................. A61K 9/70
(52) U.S. Cl. ..................... 424/449; 424/443; 424/78.02
(58) Field of Search ................................. 424/401, 400, 424/443, 447, 449, 59, 78.02, 78.03, 78.05, 78.06

(56) References Cited

U.S. PATENT DOCUMENTS 4,745,916 A 5/1988 Seber .......................... 128/155
4,784,857 A * 11/1988 Berry et al. ................. 424/449
5,719,197 A * 2/1998 Kanios et al. ........... 514/772.6

FOREIGN PATENT DOCUMENTS

| FR | 2184498 | 12/1973 |
| WO | WO 95 07077 | 3/1995 |
| WO | WO 9809155 | 3/1998 |

OTHER PUBLICATIONS

English abstract of JP 59039827, Mar. 5, 1984; Y. Toshiyuki.

* cited by examiner

Primary Examiner—Jose' G. Dees
Assistant Examiner—Konata M George
(74) Attorney, Agent, or Firm—Birch, Stewart, Kolasch & Birch, LLP

(57) ABSTRACT

The invention relates to a device for protecting a skin area against light when detecting and/or treating skin disorders, especially cancer and its preliminary stages, including application of compounds and/or compositions to the skin, in connection with which a photoreactive substance appears in the skin area. The device comprises an opaque foil (1) forming a cavity (4) relative to the skin and having edges (3) engaging the skin, the width of the edges (3) being determined by formula (I), wherein m=the width of the edge, $\delta$=the penetration depth of the light in the skin, ln=the natural logarithm, t=the time of the effect of the light, $I_0$=the luminous intensity at the skin surface, and $D_{diffused}$=the diffused energy dose which is allowed to reach the skin area concerned.

12 Claims, 1 Drawing Sheet

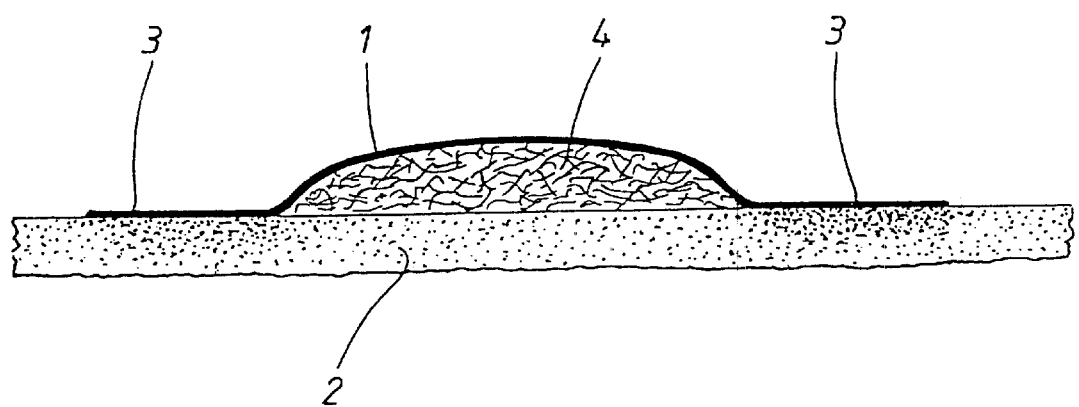

DEVICE FOR PROTECTION AGAINST THE SUN AND APPLICATION OF SUBSTANCE TO THE SKIN

This application is the national phase under 35 U.S.C. § 371 of PCT International Application No. PCT/SE99/01154 which has an International filing date of Jun. 24, 1999, which designated the United States of America.

TECHNICAL AREA

The present invention relates to a device for protecting a skin area against light when detecting and/or treating skin disorders, especially cancer and its preliminary stages, including application of compounds and/or compositions to the skin, in connection with which a photoreactive substance appears in the skin area.

BACKGROUND ART

Skin cancer may be detected optically by applying a gel, ointment or the like containing deltaaminolevulinic acid (ALA) to the skin area and letting this mixture act on the skin from 1 to 24 h, after which the ALA mixture is removed. In the skin, ALA is transformed into protoporphyrin IX. When the ALA substance has been allowed to act on the skin, protoporphyrin IX has formed in greater quantities in those parts of the skin area where there is a skin disorder than in the rest of the skin area. Then the skin area is illuminated by light of a certain wavelength and intensity. Protoporphyrin IX has such properties that those parts of the skin area which have a skin disorder and thus contain a particularly high concentration of the substance, will fluoresce with higher intensity than the other parts of the skin area. The fluorescence is registered by means of a camera and is evaluated. In order to obtain good and reliable results, the radiation needs a certain wavelength, and the chamber which catches the fluorescent radiation must also have the requisite filters so that only light of a certain wavelength will be registered. ALA, which is easily soluble in water, is applied in an oil-in-water or water-in-oil form or as a gel. Usually, a nurse applies ALA to the patients to be examined, but the patients themselves may also apply ALA at home and bandage up the site of application, and then after a few hours they go to the hospital for detecting of cancer. This whole cancer detection method is described in Swedish patent 9603095-2.

By using ALA, it is also possible to directly attack the changed skin cells, for example cancer cells, by special light treatment of the skin area, which gives rise to phototoxic reactions originating from protoporphyrin IX.

Whether such treatment takes place or not, the skin is sensitive to light after the removal of superfluous gel, even some time after the detection procedure.

The purpose of applying compounds or compositions comprising ALA is thus to prepare the skin area for subsequent detection of skin disorders, especially cancer and its preliminary stages, by means of fluorescent light and/or to treat the area with light, a phototoxic reaction taking place which is injurious to the changed cells, for instance cancer cells.

TECHNICAL PROBLEM

The very application itself of compounds and/or compositions, such as ALA, to the skin in the above-described manner is easy and causes no problems. However, there is a difficulty since light has to be shut out from the skin area to which compounds and/or compositions have been applied so that no unwanted photoreactions will take place. These unwanted phototoxic reactions result in uncontrolled treatment and bleaching and may take place both before and after the detection procedure. It is also important that the compounds and/or compositions are applied in correct quantities and that the skin area is not disturbed during or after the treatment with compounds and compositions.

Solution

The present invention has thus solved the above problem in protection of the area at issue against light and provided a device for protecting a skin area against light in connection with detection or treatment of skin disorders including application of compounds and/or compositions to the skin, in connection with which a photoreactive substance appears in the skin area, the device being characterised in that it comprises an opaque foil forming a cavity relative to the skin and having edges engaging the skin, the width of the edges being determined by the formula:

$$m > \delta \cdot \ln\left(\frac{t \cdot I_0}{D_{diffused}}\right)$$

wherein
  m=the width of the edge,
  δ=the penetration depth of the light in the skin,
  ln=the natural logarithm,
  t=the time of the effect of the light,
  $I_0$=the luminous intensity at the skin surface, and
  $D_{diffused}$=the diffused energy dose which is allowed to reach the skin area to which ALA is applied.

Such a device limits the dose of photoactivating luminous energy that is diffused under the edges and into the area of treatment. The frequent light which has the greatest penetration depth is to be found in the red area of the visible spectrum and may, for example, have a wavelength of 600–650 nm.

It is suitable that the diffused energy dose is below, for example, 0.2 J/cm² to prevent an unwanted photoactive effect on the skin. The width of the edges may then be 10–20 mm.

Preferably, the photoreactive substance can be protoporphyrin IX, the properties of which are relatively well known.

Conveniently, compounds and/or compositions containing deltaaminolevulinic acid (ALA) may be applied to the skin.

An example of compositions comprising ALA is a cream or a gel which contains an ALA compound. Another example is deltaaminolevulinic acid itself.

According to the invention, it is suitable that the foil is formable and consists of metal, metal on plastic or opaque plastic. It is also advantageous if the foil is made of a heat-insulating material, for example metal foil. This gives a higher temperature in the skin area concerned, which results in a better blood supply, and thus oxygen supply to the same. Since oxygen is essential for the phototoxic effect used for the detection, such a plaster contributes to the efficiency of the treatment. The higher temperature also has a favourable effect on the formation of protoporphyrin IX.

Such a device can be used as an application and protection device for applying compositions and/or compounds to the skin, and protecting the area at issue against sunlight before and after the detection procedure.

When the device is intended to be used for the application of a certain substance, i.e. a composition and/or compounds in connection with which a photoreactive substance appears on the skin before detection and an optional treatment, the cavity formed relative to the skin preferably contains the substance to be applied to the skin. The fact that the application takes place in this way ensures that no substance will get outside of the desired area, for instance, under the edges of the device or completely outside of the device. Such a misplaced substance would be more or less unprotected against light and might then cause skin injuries.

DESCRIPTION OF FIGURES

In the following, the invention will be described in more detail with reference to the accompanying FIGURE, which is a sectional view of the device according to the invention applied to a skin area.

DETAILED DESCRIPTION

The FIGURE shows the device according to the present invention with a casing 1, which is applied to the skin 2 and which has edges 3 engaging the skin 2. The edges 3 may be attached by gluing or by applying a bandage on the top of the same. The casing 1, which constitutes the main part of the device according to the invention, conveniently consists of metal foil, a metal on a plastic foil or opaque plastic, for instance black plastic. Suitably, the casing 1 is formed in advance so that a cavity 4 is created between the skin 2 and the foil 1. The foil 1 also needs to be formable in situ so that the device may be adapted to areas which are difficult to reach and cover, for example adjacent to or on the nose, near the eye etc. Conveniently, the foil 1 can be thermally insulating in such manner that the temperature in the skin area under the device is kept high. A high temperature entails a good circulation of blood in the skin area, which results in a higher oxygen concentration. The high oxygen concentration speeds up the phototoxic reactions in connection with subsequent illumination of the skin area. The higher temperature also has a favourable influence on the formation of protoporphyrin IX.

The cavity 4 in the device may be filled with foam plastic, cotton wool or the like, which is capable of retaining the ALA solution. It may also be filled with only a cream or gel containing ALA. The cavity 4 may be covered with protective plastic, which is removed before adding ALA. The device may be made in advance containing ALA in the cavity 4, but alternatively the ALA solution is introduced into the cavity 4 just before the device according to the invention is applied to the skin. The ALA solution, which is available in an oil-in-water emulsion or a water-in-oil emulsion, conveniently has an ALA concentration of 5 to 25%.

The size of the edges 3 of the device is extremely important to the required result. They have to be so big that light is not diffused in the skin and into the area which is treated with ALA with a view to preventing high and uncontrolled doses of photoactivating light during the treatment.

If the total dose of light which is diffused into the area of treatment is lower than 0.2 J/cm², no serious injury will arise in the area treated with ALA. Thus, the energy in the light which is diffused under the edge, should not exceed 0.2 J/cm² during the time of treatment.

The energy which is diffused under the edge is determined by the intensity I of the light which hits the skin outside of the edges 3, the time of the skin exposure t, the penetration depth $\delta$ of the light and the width m of the opaque edge 3.

The dose which is diffused under the edge is determined by the expression. Thus, the size $D_{diffused}$ should be less than 0.2 J/cm².

$$D_{diffused} = t \cdot I_0 \cdot e^{\frac{-m}{\delta}}$$

Consequently, the width of m can be determined by the above formula, which in its calculated state yields $$m > \delta \cdot \ln\left(\frac{t \cdot I_0}{D_{diffused}}\right)$$

This gives a width of the edges 3 of 10 to 20 mm in normal states, for example in sunlight.

After detection and/or treatment comprising application of compounds and/or compositions containing ALA, a device similar to the one described above can be used, but this time without ALA in the cavity 4 and only with a compress or the like. The area is thus protected from light some time after the detection since residues of ALA or protoporphyrin IX may be left in the skin.

The invention is not limited to the shown embodiment and may be varied in different ways within the scope of the claims. For instance, the form of the device may be varied to fit different parts of the body. Even though ALA is used in the described example, also other compositions and/or compounds may be used, in the application of which to the skin a photoreactive substance appears. Also other photoreactive substances than protoporphyrin IX may be used.

What is claimed is:

1. A device for protecting a skin area against light when detecting and/or treating skin disorders, including application of at least one of compounds and compositions to the skin, in connection with which a photoreactive substance appears in the skin area, wherein the device comprises an opaque foil forming a cavity relative to the skin and having edges engaging the skin, the width of the edges being determined by the formula:

$m > \delta \cdot \ln(t \cdot I_0 / D_{diffused})$ wherein
   m=the width of the edge,
   $\delta$=the penetration depth of the light in the skin,
   ln=the natural logarithm,
   t=the time of the effect of the light,
   $I_0$=the luminous intensity at the skin surface, and
   $D_{diffused}$=the diffused energy dose which is allowed to reach the skin area concerned.

2. The device as claimed in claim 1, wherein the photoreactive substance is protoporphyrin IX.

3. The device as claimed in claim 1, wherein compounds and/or compositions contained deltaaminolevulinic acid (ALA) is applied to the skin.

4. The device as claimed in claim 1, wherein the foil is formable and consists of metal, metal on plastic or opaque plastic.

5. The device as claimed in claim 1, wherein the foil is made of a heat-insulating material.

6. The device as claimed in claim 1, wherein the cavity formed relative to the skin contains compounds and/or compositions to be applied to the skin.

7. The device as claimed in claim 6, wherein the cavity formed relative to the skin contains an absorbent material that is capable of retaining the compounds and/or the compositions.

8. The device as claimed in claim 1, wherein the cavity formed relative to the skin contains a protective material protecting the skin after at least one of detection and treatment.

9. The device as claimed in claim 1, wherein the dose of photoactive luminous energy which is diffused under the edges and into the area of treatment is below 0.2 J/cm$^2$.

10. The device as claimed in claim 1, wherein the width of the edges is 10–20 mm.

11. The device as claimed in claim 1, wherein the cavity is covered with protective plastic which is removed before use of the device.

12. The device as claimed in claim 1, wherein the skin disorders the device protects against include cancer and preliminary stages thereof.

* * * * *